United States Patent
Niehr et al.

(10) Patent No.: US 9,505,598 B2
(45) Date of Patent: Nov. 29, 2016

(54) DEVICE AND METHOD FOR THE STERILIZATION OF SEALS FOR CONTAINERS

(71) Applicant: KHS GmbH, Dortmund (DE)

(72) Inventors: Thomas Niehr, Bad Münster am Stein Ebernburg (DE); Jürgen Vorwerk, Mörsdorf (DE); Igor Singur, Bad Kreuznach (DE)

(73) Assignee: KHS GmbH, Dortmund (DE)

( * ) Notice: Subject to any disclaimer, the term of this patent is extended or adjusted under 35 U.S.C. 154(b) by 0 days.

(21) Appl. No.: 14/427,419

(22) PCT Filed: Aug. 24, 2013

(86) PCT No.: PCT/EP2013/002554
§ 371 (c)(1),
(2) Date: Mar. 11, 2015

(87) PCT Pub. No.: WO2014/040694
PCT Pub. Date: Mar. 20, 2014

(65) Prior Publication Data
US 2015/0246801 A1    Sep. 3, 2015

(30) Foreign Application Priority Data
Sep. 11, 2012   (DE) .................. 10 2012 017 986

(51) Int. Cl.
*A61L 2/00* (2006.01)
*B67B 3/00* (2006.01)
*A61L 2/20* (2006.01)
*A61L 2/18* (2006.01)

(52) U.S. Cl.
CPC .............. *B67B 3/003* (2013.01); *A61L 2/186* (2013.01); *A61L 2/20* (2013.01); *A61L 2202/23* (2013.01)

(58) Field of Classification Search
CPC .................................. A61L 2/00; A61L 2/18
USPC ..................... 422/28, 292, 300, 307
See application file for complete search history.

(56) References Cited

U.S. PATENT DOCUMENTS

2011/0142731 A1 * 6/2011 Beckmann et al. .... A61L 2/208
422/292

FOREIGN PATENT DOCUMENTS

| DE | 198 51 654 | 5/2000 |
|---|---|---|
| DE | 10 2008 048351 | 4/2010 |
| DE | 10 2010 025541 | 12/2011 |
| DE | 10 2010 052207 | 5/2012 |
| EP | 1 801 066 | 6/2007 |
| WO | WO 2010/031464 | 3/2010 |

* cited by examiner

*Primary Examiner* — Monzer R Chorbaji
(74) *Attorney, Agent, or Firm* — Occhiuti & Rohlicek LLP (57) ABSTRACT

A sterilizing machine for sterilizing bottle seals includes a rotor with vertically-oriented seal holders disposed on its periphery. Each seal holder accommodates a seal stack. As the rotor rotates, the seal holder carries the stack from a seal input, past first and second stations, to a seal output. The first station has a sterilizing-agent sprayer with successive outlets spaced apart from each other in the longitudinal direction by one seal diameter. The sprayer is directed toward a seal holder for applying sterilizing agent onto individual seals held therein. The second station is an activating and/or drying station downstream of the first station in the rotation direction.

13 Claims, 4 Drawing Sheets

DEVICE AND METHOD FOR THE STERILIZATION OF SEALS FOR CONTAINERS

RELATED APPLICATIONS

This application is the national stage entry under 35 USC 371 of international application PCT/EP2013/002554, filed on Aug. 24, 2013, which claims the benefit of the Sep. 11, 2012 priority date of German application DE 102012017986.3, the contents of which are herein incorporated by reference.

FIELD OF INVENTION

The invention relates to containers for beverages, and in particular, to disinfection and sterilization of seals for such containers.

BACKGROUND

Within the beverage industry, it is known to seal filled bottles or other containers with some sort of seal. These seals include, in particular cap-like seals such as screw caps, flat caps, and crown stoppers. These seals are typically sterilized or disinfected before being placed on a container. A common way to sterilize these seals is to use sterilizing-agents consisting of $H_2O_2$ vapor or a gaseous and/or vaporous carrier medium enriched with $H_2O_2$ aerosol.

To achieve effective sterilization with a high sterilization rate, it is known to preheat the seals before applying sterilizing-agent. The seals are typically preheated to be within a temperature ranging between 50° C. and 85° C. After the treatment or application of the gaseous and/or vaporous sterilizing-agent, the caps are dried with the use of a preferably heated sterile gaseous and/or vaporous medium, for example with heated sterile air. The sterilized seals, which are by this point suitable for sealing of containers, are then passed to a sealing machine for this purpose.

A known device for the sterilization of seals for containers with $H_2O_2$ aerosol or steam has two rotors driven to circulate around a common vertical machine axis. Each rotor is accommodated in a treatment space. On each rotor, seal-holders are distributed about the machine axis. Each seal-holder holds many seals in a row and extends in an axial direction parallel to a machine axis. As the rotors circulate, the seals move with the seal-holders through treatment spaces between a seal-input and a seal-output. In each of the treatment spaces, the seals are sprayed with hot air. This exposure to hot air is carried out specifically to preheat the seals in the treatment space of the upper rotor, to activate the sterilization medium in the treatment space of the lower rotor, and to dry the seals. The actual spraying of sterilization medium on the seals occurs on a treatment path that is oriented parallel to the machine axis and that connects the seal-output of the upper rotor with the seal-input of the lower rotor. Seals move through this treatment path under the influence of gravity.

A device of this type has two rotors, and is therefore quite large. Additionally, the treatment time for spraying the seals with the sterilizing-agent and also the dwell time of the cycled movement of the rotors depend on the velocity at which the seals fall through the treatment path. A further problem with these sterilization units is that once warmed, the seals soften and lose stability of form. This can subsequently lead to mechanical faults in the course of transport and as the seals move freely among one another.

Also known are devices that sterilize seals with UV radiation. In known devices of this type, seals are held in vertically aligned cage-like seal-holders that are formed on the periphery of a rotor that can be driven to rotate about a vertical machine axis. These seal-holders are oriented with their longitudinal extension parallel to the rotor axis. The seals move with the rotor or with the seal-holders on a treatment path between a seal-input and a seal-output past a plurality of UV radiators that do not circulate with the rotor.

SUMMARY

The invention provides a device that facilitates high sterilization quality and/or a disinfection rate, thus ensuring targeted sterilization of individual seals with a high, uninterrupted throughput.

In one aspect, the invention features an apparatus for processing seals that are used for closing bottles. Such an apparatus include a sterilizing machine for sterilizing the seals. The sterilizing machine has a transport system for moving the seals through treatment zones in which the seals are sterilized, activated, and dried. The transport system includes a seal-input, a seal-output, a rotor, a treatment path, a first application station, an activation-and/or-drying station, and seal-holders disposed on the rotor's periphery. The rotor rotates about a rotor axis in a rotation direction. The seal-holders are vertically oriented and extend along a longitudinal direction. Each of the seal-holders accommodates a stack of seals, which it carries along the rotation direction through the treatment zones on the treatment path between the seal-input and the seal-output. The first application station, which is on the treatment path, includes a first sterilizing-agent sprayer, with successive outlets spaced apart from each other in the longitudinal direction by an amount that is equal to, or substantially equal to, the diameter of the seals. The first sterilizing-agent sprayer is directed toward a seal-holder for applying sterilizing-agent onto individual seals held therein. The activating and/or drying station is provided downstream of the first application station in the rotation direction.

Some embodiments include a second sterilizing-agent sprayer positioned opposite the first sterilizing-agent sprayer. The first and second sterilizing-agent sprayers are configured to apply sterilizing-agent to opposite sides of individual seals that are held in a seal-holder.

Other embodiments include a second application station for applying the sterilizing-agent to seals that are held in seal-holders. The second application station follows the first application station in the rotation direction.

In other embodiments, the seal-holders are distributed about the rotor axis, with each pair of successive seal-holders being separated by a fixed angular distance. Each pair of successive application stations includes application stations that are spaced apart by at least twice the fixed angular distance. These embodiments include those with a central sterilizing-agent supply that interconnects outlets of sterilizing-agent spraying-devices from different application stations.

Other embodiments include a waiting station disposed downstream of the application station and upstream of the activation and/or drying station in the rotation direction.

Yet other embodiments feature a cooling station downstream of the activating and/or drying station in the rotation direction.

In some embodiments, the rotor includes a hollow drum. The seal-holders are arranged to form a cage with rod-like or bar-like seal guide rails that collectively define a drum jacket for the hollow drum. The guide rails extend along the longitudinal direction and are disposed to receive seals into the seal-holders by having the seals pass between the guide rails.

In other embodiments, the seal-holders are oriented with their longitudinal directions parallel to the rotor axis.

In yet other embodiments, the first sterilizing-agent sprayer is disposed to be lying inside or outside along a trajectory of the seal-holders. In these embodiments, the first sterilizing-agent sprayer does not circulate with either the seal-holders or the rotor.

Additional embodiments are those in which the rotor defines a hollow drum. In these embodiments, the apparatus further comprises central gas pipes and gas regulating devices connected to the gas pipes for gas and atmosphere management in the drum's interior.

In another aspect, the invention features a method for sterilizing seals. Such a method includes, at a seal-input, placing a stack of seals in a vertically oriented seal-holder on a periphery of a rotor that moves the seal-holder, along with the seals, in a rotation direction along a treatment path, bringing the stack of seals to a first application station on the treatment path, at the first application station, directing sterilizing-agent toward the seal-holder for applying sterilizing-agent onto individual seals held therein, wherein directing sterilizing-agent includes passing the sterilizing-agent through successive outlets of a first sterilizing-agent sprayer, the outlets being spaced apart from each other by a seal diameter in the longitudinal direction, moving the stack of seals downstream along the rotation direction, activating or drying the stack of seals, and moving the stack of seals downstream to a seal outlet.

In another aspect, the invention features a sterilizing machine for sterilizing bottle seals. The machine includes a rotor with vertically-oriented seal-holders disposed on its periphery. Each seal-holder accommodates a seal stack. As the rotor rotates, the seal-holder carries the stack from a seal-input, past first and second stations, to a seal-output. The first station has a sterilizing-agent sprayer with successive outlets spaced apart from each other in the longitudinal direction by one seal diameter. The sprayer is directed toward a seal-holder for applying sterilizing-agent onto individual seals held therein. The second station is an activating-and/or-drying station downstream of the first station in the rotation direction.

In yet another aspect, the invention features a device for the sterilization of seals for closing bottles or similar containers, in particular for the sterilization of cap-like seals, with a transport system for moving the seals through a plurality of treatment zones in which the seals are sterilized as well as activated and/or dried. In at least one treatment zone the transport system has at least one rotor that can be driven to rotate about a machine or rotor axis and that has a plurality of seal-holders configured on the periphery of the said rotor. These seal-holders move the seals through a plurality of treatment zones on a treatment path between a seal-input and a seal-output. One or more application stations are provided on the treatment path. Each one has a sterilizing-agent spraying-device that is directed toward at least one seal-holder for the controlled and/or targeted application of sterilizing-agent on the individual seals received and held in the seal-holder. The sterilizing-agent is typically hydrogen peroxide aerosol or vapor, a sterilizing-agent containing hydrogen peroxide aerosol, and/or a gas for activating the hydrogen peroxide and/or for drying the surfaces.

Among the particular advantages are that a group of seals is held at rest in the seal-holders, i.e. the seals in the seal-holders move neither relative to one another nor to the seal-holder itself during the entire treatment time. An absolutely uninterrupted flow of the seals is facilitated through this simple guiding of the seals during the treatment. This results in a high-throughput despite the very compact design and small overall volume. In particular, high disinfection rates are consistently achieved during sterilization.

As used herein, the term "seal" is understood to refer to many different types of seals, in particular cap-like seals such as screw caps, flat caps, crown stoppers, etc.

The term "hydrogen peroxide aerosol or $H_2O_2$ aerosol" is understood in the following text to refer to a mixture that contains at least a carrier gas, in particular air, as well as $H_2O_2$ or an $H_2O_2$-bearing liquid, in particular an aqueous solution. The $H_2O_2$ or the $H_2O_2$ solution can have been introduced into or be present in the carrier gas atomized (e.g. by way of a nozzle) and/or evaporated by the application of energy and mixed in it. A hot hydrogen peroxide aerosol is preferably used.

In a preferred embodiment, at least two sterilizing-agent spraying-devices lying opposite one another are provided at an application station. The two sterilizing-agent spraying-devices are configured for the targeted spraying of the individual seals held in a seal-holder with hydrogen peroxide aerosol from opposite sides. As a consequence, as complete a spraying as possible of the surface of the seals with sterilizing-agent, and hence optimum sterilizing action, is achieved.

In a preferred embodiment, application stations for the targeted spraying of the seals held in the seal-holders with hydrogen peroxide aerosol are provided following one another in the direction of circulation of the rotor. As a result the application operation can be carried out in a plurality of steps that are chronologically separate from each other, thereby providing a further increase in the quality of sterilization.

Preferably the seal-holders are distributed at fixed angular or pitch distances about the machine or rotor axis and successive application stations are spaced apart from one another by at least two angular or pitch distances. In the case of a cycled, i.e. intermittent, rotary motion of the rotor by one angular or pitch distance per cycle, the treatment of the seals contained in a seal-holder at the first application station is followed by a dwell time of the seals lasting at least one cycle time at an acting or waiting station that is disposed between the application stations. The sterilizing-agent can act on the seals during this time.

After a further cycled rotary motion of the rotor, these seals are passed to the second application station, where sterilizing-agent is once again applied to the seals. The quality of sterilization is further improved by spacing the application stations apart from one another.

In another embodiment, the sterilizing-agent spraying-device has a plurality of outlets, with successive outlets being spaced apart by one seal diameter or substantially one seal diameter in the direction of the longitudinal extension of the seal-holders.

In another embodiment, the outlets are arranged such that they each come to rest centrally, i.e. on the same axis, or substantially centrally, i.e. almost on the same axis, relative to the seals provided in the seal-holders. This ensures that one outlet is associated with each of the seals and that therefore that sterilizing-agent is applied individually and selectively to each seal.

In another embodiment, individual outlets of the sterilizing-agent spraying-device and/or the sterilizing-agent spraying-devices of different application stations are interconnected by way of a central sterilizing-agent supply. This makes possible the central feeding of all outlets of the sterilizing-agent spraying-devices by way of a single sterilizing-agent supply.

Preferably at least one activating-and/or-drying station is provided following an application station in the direction of rotation. At this activating-and/or-drying station the seals are dried with a drying-and-activating medium, preferably with the use of heated sterile air. Associating one nozzle with each seal results in more effective drying by targeting each seal individually with the drying air.

Particularly at the beginning of the application of the drying-and-activating medium to the seal, this drying of the seals brings about an activating of the hydrogen peroxide ($H_2O_2$) present in the sterilizing medium, thus breaking it down into its decomposition products and bringing about the sterilization.

Some embodiments have an acting station downstream of the application station and upstream of the activating and/or drying station. This acting station provides a waiting time between application of the sterilizing medium and drying and/or activating. The waiting time allows the sterilizing-agent to act on the seals over an extended period.

In some embodiments, the rotor is configured as a hollow drum or hollow cylinder having a cage-like drum envelope formed with a plurality of seal-holders. Each of the seal-holders is configured as a cage having rod-shaped and/or bar-shaped seal guide rails that extend in the longitudinal direction of the seal-holder and between which the seals are accommodated in the seal-holder. As a result of this arrangement, the seals present in the seal-holders lie almost completely exposed and so can be sprayed with sterilizing-agent.

In some embodiments, the seal-holders are oriented with their longitudinal extension in the direction of the rotor axis, preferably parallel or substantially parallel to the rotor axis. As a result of this, as the rotor rotates, the seals, which are contained and arranged in rows in the seal-holders, are conveyed past the treatment stations, in particular the sterilizing-agent spraying-devices, and in the process can undergo the sterilization steps. The sterilizing-agent spraying-devices are preferably provided lying on the inside and/or outside along the trajectory of the seal-holders but not circulating with these seal-holders or with the rotor.

In other embodiments, a seal contact surface lies opposite a lower open end of the seal-holders. This seal contact surface is not moved with the rotor. As the rotor rotates, the seal adjacent to this seal contact surface rolls. This rotates the seal, which transmits this rotary motion to the seals adjacent to it. In this way, rotary motion is transmitted from seal to seal. The rotary motion of the lowest seal held in a seal-holder is thus transmitted to the seals lying above it, so setting the latter to rotate in pairs in different directions. This rotary motion prevents regions of the seals, in particular regions that lie behind the seal guide rails, from not being sprayed with sterilizing-agent.

As used herein, "substantially" means variations from an exact value by ±10%, preferably by ±5%, and/or variations that are insignificant to function.

The specification refers to "upstream" and "downstream" directions. These are defined relative to a direction of rotation. The rotation direction defines a velocity vector. A first point is said to be upstream of a second point if the displacement vector that must be added to the coordinates of the first point to bring it to the second point is in the same direction as the velocity vector. A first point is said to be downstream of the second point if the converse is true.

Further embodiments, advantages and possible applications of the invention arise out of the following description of embodiments and the figures. All of the described and/or pictorially represented attributes, whether alone or in any desired combination are fundamentally the subject matter of the invention independently of their synopsis in the claims or a retroactive application thereof. The content of the claims is also made an integral part of the description.

BRIEF DESCRIPTION OF THE DRAWINGS

These and other features and advantages of the invention will be apparent from the following detailed description and the figures, in which.

DETAILED DESCRIPTION

Figure 1:
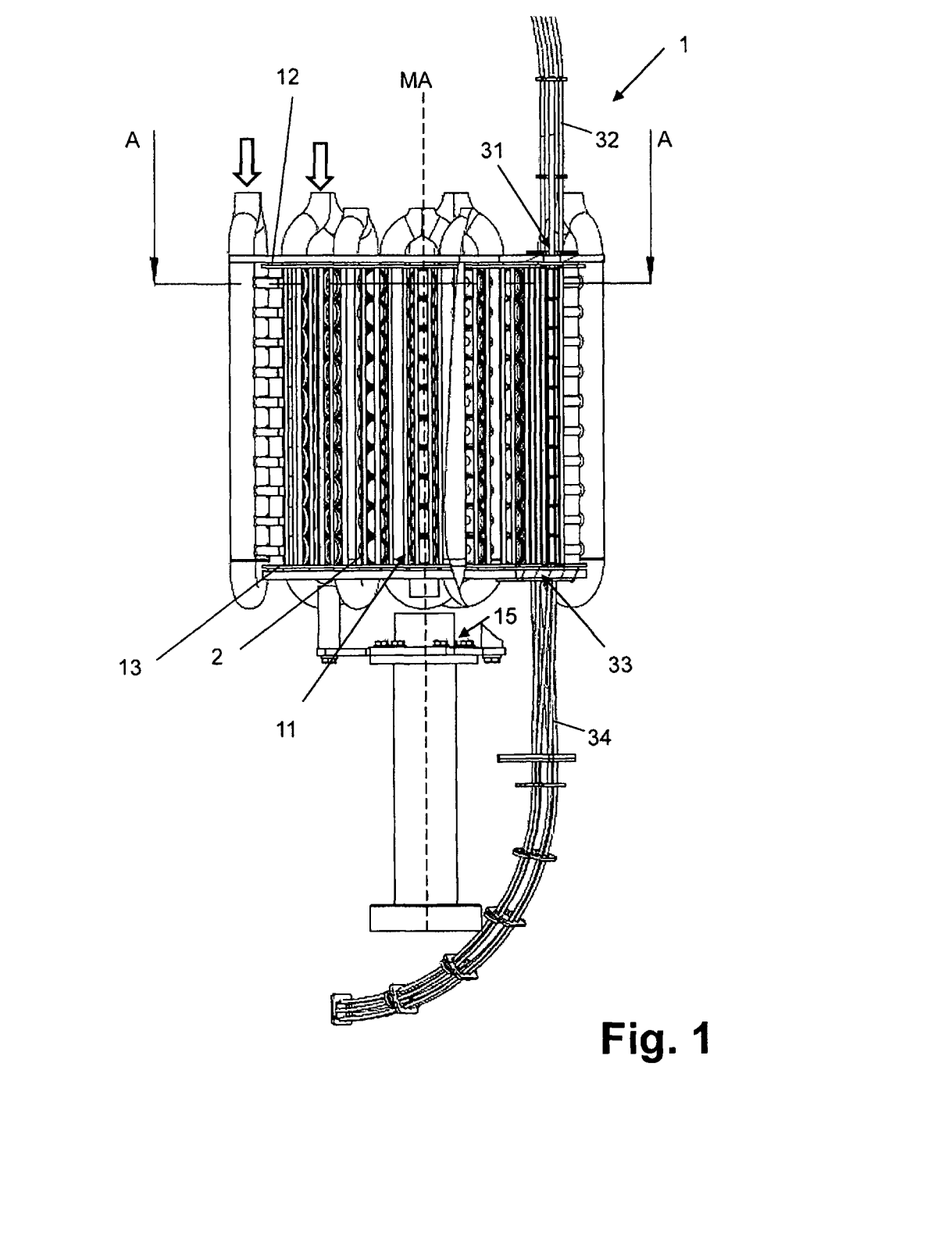
FIG. 1 shows a lateral view of an inventive device for the sterilization of seals with sterilizing-agent.

FIG. 1 shows a seal-sterilizing device 1 for sterilization and/or disinfection of seals 2. These seals are used to cap containers, such as bottles. Typical seals are caps, screw caps, sport caps, flat caps or crown stoppers etc. The seal-sterilizing device 1 is typically placed upstream of a sealing machine. In operation, the seal-sterilizing device 1 passes sterilized seals 2 under sterile and/or aseptic conditions to the sealing machine, which then seals the containers.

The seal-sterilizing device 1 comprises a housing or enclosure, which has been omitted from the figures for clarity. The housing has a polygonal or cylindrical shape surrounding a vertical machine axis or rotor axis MA. In one embodiment, the housing is hexagonal.

With the exception of inlets and outlets for enabling passage of seals 2, the interior of the housing is sealed tightly against the exterior by an outer wall that encloses the machine axis MA, by an upper housing wall, and a lower housing wall. Inspection windows can be provided in the outer wall. Alternatively, the entire outer wall of the housing can be made of a transparent material.

The interior of the housing accommodates a rotor 10 that can be driven for incremental rotation about a vertical machine axis MA. In the illustrated embodiment, the rotor 10 is a hollow drum in the form of a circular cylinder that concentrically encloses the machine axis MA. The drum has a drum jacket with a cage formed by seal-holders 11, each of which accommodates a plurality of seals 2 in a row. The drum jacket is an inherently stable jacket that can also be described as mesh-like Each seal-holder 11 is oriented with its longitudinal extension parallel or substantially parallel to the machine axis MA. Each seal-holder 11 is open at its upper end for receiving seals 2 and at its lower end for discharging seals 2. The seal-holders 11 collectively form the jacket of the rotor 10. To facilitate formation of the jacket, the seal-holders 11 are distributed around the periphery of the rotor 10 at equal angular and pitch distances around the machine axis MA.

Each seal-holder 11 has an upper end and a lower end. The upper end of a seal-holder 11 attaches to an annular upper carrier-element 12. The lower end of a seal-holder 11 attaches to an annular lower carrier-element 13. The annular upper and lower carrier-elements 12, 13 are arranged concentrically with the machine axis MA. Each seal-holder 11 is attached in such a way that its lower open end remains uncovered by the lower carrier-element 13. The lower end of a seal-holder 11 instead lies exposed in the region of the lower carrier-element 13 or beneath that lower carrier-element 13.

Each seal-holder 11 is also configured in the manner of a mesh. In particular, each seal-holder 11 has rod-like and/or bar-like seal guide rails 14 spaced apart from one another and oriented parallel to the machine axis MA. The guide rails 14 form between them a receiving space in which to receive seals 2. The seals 2 in each seal-holder 11 form a single-track row or group of seals extending in an axial direction parallel to the machine axis MA. This defines a stack of seals 2.

Within a seal-holder 11, the seals 2 lie as exposed as possible. In particular, the guide rails 14 cover the seals 2 over a minimal portion of their surface only. The seal-holders 11 can also be manufactured as milled parts with appropriately adapted contours to maximize exposure of seals 2 contained therein.

A seal 2 defines a seal axis that is normal to the face of the seal. The seal holders 11 are configured such that seals 2 in a seal-holder 11 are oriented with their respective seal axes extending in a radial direction relative to the machine axis MA with the open side of the seal 2 oriented to face radially outward.

Figure 3:
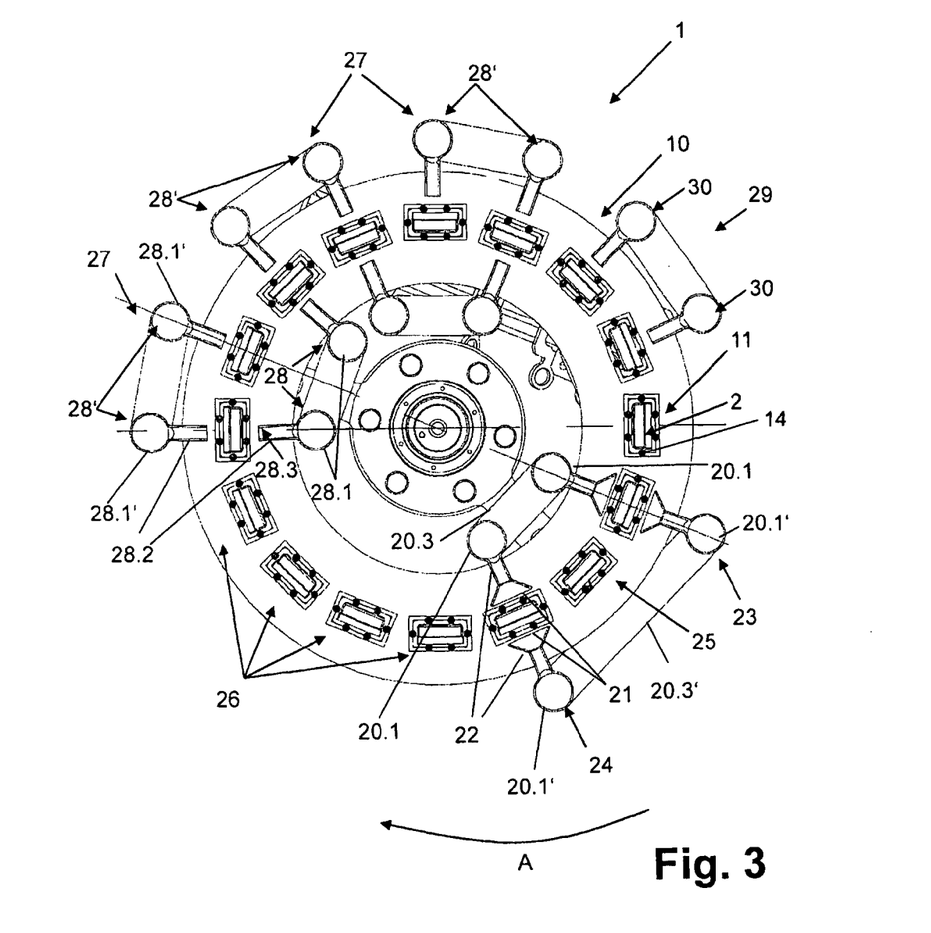
FIG. 3 shows a sectional view of the device of FIG. 1 on section A-A.

The rotor 10 is mounted with the lower carrier-element 13 in a bearing 15 on the underside of the seal-sterilizing device 1 so as to be able to rotate about the machine axis MA and to be driven to rotate in steps, cycles and/or increments about the machine axis MA along a rotation direction A, shown in FIG. 3, by way of a drive, such as an electric motor with a gearbox.

Sterilizing-agent spraying-devices 20, 20', which do not rotate with the rotor 10, are provided preferably in the interior of the housing within the treatment space of the seal-sterilizing device 1. The sterilizing-agent spraying-devices 20, 20' are preferably oriented with their longitudinal extensions each parallel to the machine axis MA.

The illustrated embodiment has two pairs of sterilizing-agent spraying-devices 20, 20'. A first sterilizing-agent spraying-device 20 of each pair is positioned adjacent to a radially inward side of the seal-holders 11. A second sterilizing-agent spraying-device 20' is positioned adjacent to a radially outward side of the seal-holders 11.

Figure 2:
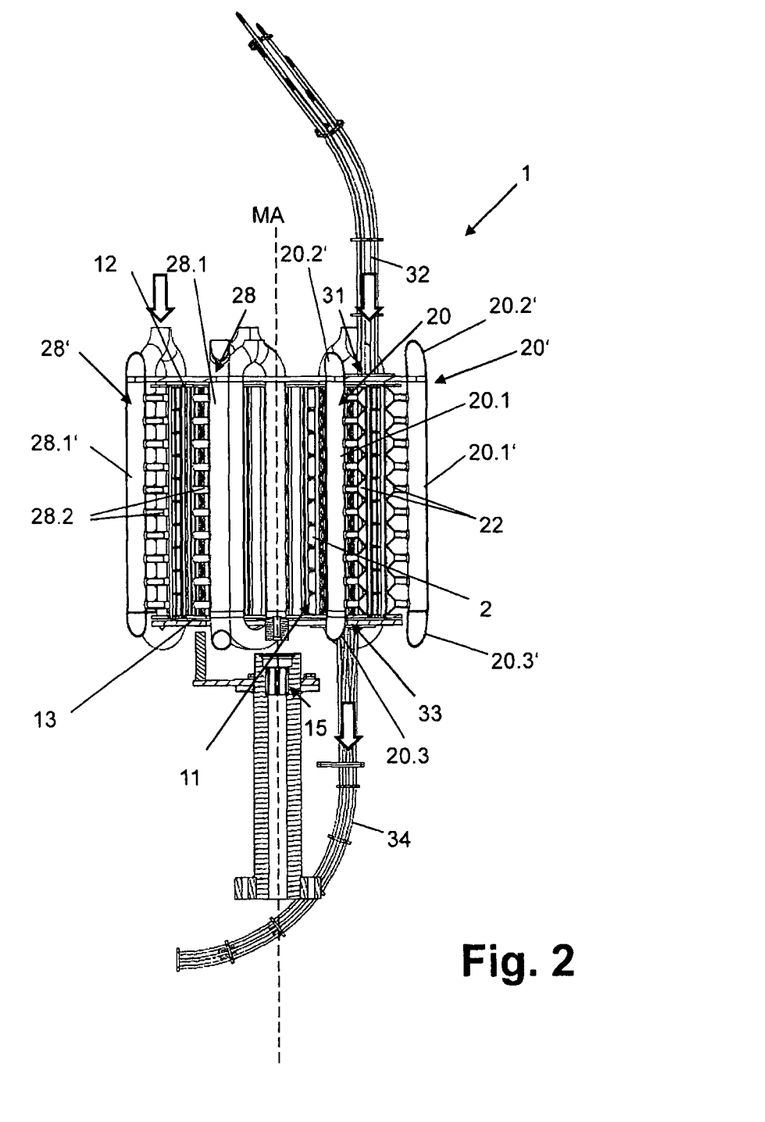
FIG. 2 shows a sectional view of the device of FIG. 1 in a sectional plane accommodating the machine axis.

Referring to FIG. 2, each sterilizing-agent spraying-devices 20, 20' includes a first spraying-device section 20.1, 20.1'. The first spraying-device section 20.1, 20.1' is configured in the form of a tube that runs parallel to the machine axis MA. On this first spraying-device section 20.1, 20.1' are provided lateral outlets 21 for the sterilizing-agent. Preferably, each sterilizing-agent spraying-device 20, 20' is also configured as a ring main so as to ensure an even supply of treatment medium to all its lateral outlets 21.

Free ends of nozzles 22 that are connected in a fluid-tight manner with the first spraying-device section 20.1, 20.1' form the outlets 21. Relative to the rotor 10, the nozzles 22 are aligned radially by their longitudinal extension. The nozzles 22 stand apart from the first spraying-device sections 20.1, 20.1' in such a way that the outlets 21 come to rest in the immediate vicinity of the seal-holders 11 that move past them as the rotor 10 rotates.

Some embodiments have first and second sterilizing-agent spraying-devices 20, 20'. The first sterilizing-agent spraying-device 20 is positioned adjacent to a radially inward-facing side of the seal-holders 11. The second sterilizing-agent spraying-device 20' is positioned adjacent to radially outward-facing side of the seal-holders 11. Preferably, nozzles 22 of the first and second sterilizing-agent spraying-devices 20, 20' have centers that are aligned with each other. A result of this alignment is that sterilizing-agent can be sprayed and/or applied simultaneously onto both the front and back of a seal 2 that is held in a seal-holder 11.

In the embodiment shown in FIG. 3, the ends of the nozzles 22 flare outward as they approach the seal-holder 11. This forms a funnel at the far end of the nozzle 22. Having nozzles 22 that form a funnel facilitates application of sterilizing-agent that covers the full area of both the front and back of seals 2.

In an alternative variant, the far ends of the nozzles 22 are spherically arched and provided with a plurality of holes. These holes promote distribution of dispensed sterilizing-agent over a wide area.

As can be seen from FIGS. 1 and 2, sterilizing-agent spraying-devices 20, 20' extend over substantially the entire longitudinal extension of the seal-holders 11 and exhibit a plurality of nozzles 22 that are distributed at some distance from each other along the length of the longitudinal extension of the seal-holder 11. The distance between successive nozzles 22 is preferably about the same as the diameter of the seals 2 that are held in the seal-holders 11. As a result, on the inside and outside of the seal-holder 11, two nozzles 22, one from each sterilizing-agent spraying-device 20, 20', are oriented directly facing opposite sides of a seal 2. Thus, each seal 2 is associated with a dedicated pair of nozzles 22. This one-to-one association between a seal 2 and a pair of nozzles 22 facilitates a thorough and targeted application of sterilizing-agent on the seal 2.

As can be seen from FIG. 3, a plurality of treatment stations for the application of the sterilizing-agent are provided on the inner and outer peripheral sides along the rotation direction A. In particular, first and second application stations 23, 24 are provided, each of which has, arranged therein, first and second sterilizing-agent spraying-devices 20, 20' lying opposite one another. As shown in FIG. 3, the first sterilizing-agent spraying-device 20' lies radially outward relative to the seal-holder 11 and the second sterilizing-agent spraying-device 20 lies radially inward relative to the seal-holder 11.

The first spraying-device sections 20.1' of the radially-outward sterilizing-agent spraying-devices 20' are connected at their tops and bottoms by second spraying-device sections 20.2', 20.3', best seen in FIG. 2. These are configured in the manner of an arch or yoke, with a central sterilizing-agent supply being preferably effected through the second spraying-device section 20.2' disposed at the top.

Likewise, first spraying-device sections 20.1 of the radially-inward sterilizing-agent spraying-devices 20 of the first and second application stations 23, 24 are connected at their top and bottom by second spraying-device sections 20.2 configured in the manner of an arch or yoke so as to configure a ring main. This results in a very even application of sterilizing-agent by the lateral outlets.

It is also possible to apply sterilizing-agent to the seals 2 that are held in a seal-holder 11 at different times using different application stations 23, 24 that are separate from one another. This is carried out by having the rotor 10 rotate intermittently. The rotor 10 first brings the seal-holder 11 to a first application station 23 and waits for one cycle-time while the sterilizing-agent spraying-devices 20 bath the seals 2 in sterilizing-agent. Then, the rotor 10 brings the same seal-holder 11 to a second application station 24 and does the same thing. The angular amount by which rotor 10 rotates about the machine axis MA during its incremental, intermittent rotary motion is determined by the fixed angular and pitch distances at which seal-holders 11 are arranged about machine axis MA. This distance will be referred to here as one "pitch."

In the depicted embodiment, first and second application station 23, 24 are spaced by two pitches. This means that if the rotor 10 moves by one pitch and waits, a seal-holder 11 will have a rest period between the first and second application stations 23, 24. This in-between location defines a waiting station 25. During this rest period, no treatment takes place. Instead, at the waiting station 25, the sterilizing-agent that was applied to the seals 2 in the first application station 23 can act before further treatment begins at the second application station 24.

After one cycle-time lapses, the rotor 10 moves one more pitch in the rotation direction A and brings the seal-holder 11 to the second application station 24, where the seals 2 are once more bathed with sterilizing-agent. This procedure achieves a two-stage direct application of sterilizing-agent onto the individual seals 2 from preferably both sides of the seal 2.

In other embodiments, there is no intermediate waiting station 25. Instead, the seal-holder 11 proceeds directly from the first applications station 23 to the second application station 24.

The illustrated embodiment has further waiting stations 26, and in particular four waiting stations 26, that follow the second application station 24 in the direction of rotation. Following the renewed application of sterilizing-agent to the seals 2 at the second application station 24, these further waiting stations 26 again serve to optimize the disinfecting and/or sterilizing process by providing more time for the sterilizing-agent to act.

Activation-and/or-drying stations 27 follow the waiting stations 26 downstream in the rotation direction A. In the depicted embodiment, there are six such activating-and/or-drying stations 27. Seals 2 therefore have six successive cycle-times to be dried and/or activated.

An activating-and/or-drying station 27 dries seals 2 by applying a hot activating-and-drying medium, such as heated sterile air. This application dries the seals 2 and also activates the hydrogen peroxide ($H_2O_2$) present in the sterilization medium, causing it to decompose, thus thoroughly sterilizing the seals 2.

Drying devices 28 by which the drying medium is selectively applied to seals 2 present in seal-holders 11 are provided at each of activating-and/or-drying stations 27. Drying devices 28' that are positioned radially on the outside are associated with individual activating-and/or-drying stations 27. Furthermore, drying-devices 28 that are likewise associated, in part at least, with activating-and/or-drying stations 27, are provided radially on the inside in such a way that the drying medium is applied to both sides of seals 2 at least partly at activating-and/or-drying stations 27. The drying-devices 28 are thus configured in substantially the same way as the sterilizing-agent spraying-devices 20, 20'.

Each drying-device has a tube-like first drying-device section 28.1, 28.1' that is aligned parallel with the machine axis MA. Radially projecting lateral nozzles 28.2 are provided at the first drying-device section 28.1, 28.1'. Through these nozzles 28.2, activating-and-drying medium that has been carried in the tube-like first drying-device section 28.1, 28.1' can exit through outlets 28.3 and be targeted directly at individual seals 2.

The nozzles 28.2 of drying-devices 28, 28' that lie opposite one another at an activating-and/or-drying station 27 are aligned so that they are coaxial with each other along an axis that is radial relative to the machine axis MA. A targeted application of drying medium onto the front and back of each seal 2 is achieved in this way in much the same way that the seals 2 were individually targeted by sterilizing-agent spraying-devices 20, 20' at the first and second application stations 23, 24.

Just like the sterilizing-agent spraying-devices 20, 20', each drying-device 28, 28' has nozzles 28.2 that are spaced apart from one another in the direction of the longitudinal axis of the first drying-device section 28.1, 28.1' in such a way that a nozzle 28.2 is centered opposite each face of each seal 2 that is present in the seal-holder 11 in the activating-and/or-drying station 27. A nozzle 28.2 or pair of opposing nozzles is preferably associated with each seal 2 that is present in the seal-holder 11 in the activating-and/or-drying station 27. As a result, each seal 2 is selectively and individually exposed to the activating-and-drying medium.

Two cooling stations 29 are provided adjacent to the activating-and/or-drying stations 27 in the rotation direction A. The cooling stations 29 expose the previously sterilized seals 2 to sterile air. A cooling device 30, which in the depicted embodiment is configured identically in construction with the drying-device 28, 28', is provided at each of the cooling stations 29, preferably outside the periphery. The cooling device 30 can thus expose the individual seals 2, which are held in rows in the seal-holder 11, to cooling medium, in particular cooled sterile air.

Above the trajectory of the seal-holders 11, and in the rotation direction A, a lower end of an inward seal-conveying section 32 forms a seal-input 31. Seals 2 to be sterilized are fed through this seal-input 31. The inward seal-conveying section 32 is provided upstream of the first application station 23 and downstream of the cooling station 29. Seals 2 in the inward seal-conveying section 32 already have an orientation that matches their orientation in the seal-holders 11.

A seal-output 33 is provided in the region of the underside of the housing beneath the trajectory of the seal-holders 11. The seal-output 33 is formed substantially by the inlet or by an upper open end of an outward seal-conveying section 34 that, with its open end, is disposed beneath the trajectory of the seal-holders 11 of the rotor 10 where it forms the seal-output 33. Sterilized seals 2 are aseptically fed to the sealing machine (not shown) along the outward seal-conveying section 34.

In the depicted embodiment, the inward and outward seal-conveying sections 32, 34 are each formed by guide rails that receive and guide seals 2 between them. Moreover, in the depicted embodiment, and at least in the vicinity of the rotor 10, the inward and outward seal-conveying sections 32, 34 each follow a vertical path. This means that that seals 2 are moved and/or conveyed along the inward and outward seal-conveying sections 32, 34 by gravity alone.

An envelope enclosing the outward seal-conveying section 34 prevents renewed contamination of sterilized seals 2 as they make their way to the sealing machine. A positive pressure of a sterile gaseous and/or vaporous medium, for example sterile air, preferably fills the envelope.

A particular advantage of the sterilizing device described herein in its various embodiments is that the incremental operation allows the dwell time before the individual treatment stages to be very easily varied and controlled. This means that longer dwell times can be provided for seals with a very complex internal structures that are more difficult to sterilize, and a shorter dwell time can be used for simpler seals.

The seal-input 31 and the seal-output 33 are arranged at an angular distance along the rotation direction A that corresponds to an integral number of pitches. This means that whenever one seal-holder 11 is waiting with its upper open end at seal-input 31, a different seal-holder 11 is also waiting with its lower open end at the seal-output 33.

The seal output 33 should be as far downstream from the seal input 31 as possible. The separation will thus be an angle that is somewhat less than 360°, depending on the pitch. Typically, the angular spacing will be on the order of 330°. This distance achieves the longest possible treatment path and hence the longest possible treatment time for the disinfecting and/or sterilizing of seals 2 that can be achieved for a particular diameter of the rotor 10. As a result, it is possible to make the rotor 10, and hence the sterilizing machine 1, more compact.

In one embodiment, the seal input 31 is arranged above the first application station 23 and the seal-output 33 is arranged at one angular or pitch distance upstream of first application station 23.

In another embodiment, the seal-input 31 is one pitch upstream of the first application station 23, in which case the seal-output 33 will be at the last cooling device, one pitch upstream of the seal-input 31. This embodiment has the advantage that even at the application station 23, which is the first relative to direction of circulation A, the full cycle time associated with incremental movement of the rotor 10 is available for the targeted application of the sterilization medium ($H_2O_2$ aerosol) to the seals 2.

The rotor 10 is driven in cycles about the machine axis MA by a drive such that the rotor 10 executes a rotational increment equivalent to one pitch. This means that when the rotor 10 is waiting between steps, an empty seal-holder 11 is present beneath the seal-input 31 so that the seal-holder 11 has time to be fully filled with seals 11 from the inward seal-conveying section 32. The rotor 10 takes the seal-holders 11, each filled with seals 2, in steps of one pitch at a time to visit the various treatment stations along the treatment path. The seals are then treated and sterilized at the individual stations while the rotor is waiting between steps.

Whenever a seal-holder 11 reaches the seal-output 33, all sterilized seals 2 carried by that seal-holder 11 fall into the outward seal-conveying section 34. These disinfected and/or sterilized seals 2 are then conveyed for further use.

During the operation of the seal-sterilizing device 1, sterilizing-agent spraying-devices 20, 20', drying-devices 28, 28' and cooling-devices 30 are operated intermittently in a manner that conforms to the incremental rotary motion of the rotor 10. As a result, the sterilizing medium, drying medium, or cooling medium is applied during the rotor's standstill phase after each rotational step that it takes.

A particular advantage of the seal-sterilizing device 1 is that all treatment steps associated with sterilizing of seals 2, i.e. the application with the sterilizing-agent and/or $H_2O_2$ aerosol, the activating of the sterilizing-agent, the drying, and the cooling of seals 2, take place in the rotor 10 with the seals 2 disposed in seal-holders 11 being moved past the individual treatment zones along the treatment path that is formed between the seal-input 31 and the seal-output 33.

Another advantage of the seal-sterilizing device 1 is that the treatment media are applied to the front and back of the seals 2 and that each seal 2 has an associated jet that targets treatment media directly onto the seal 2. This method is used not only for the sterilizing medium but also for the hot activating-and-drying medium, at the activating-and/or-drying stations 27, and for the cooling medium, at the cooling station 29.

An alternative embodiment is configured to use a different liquid or vaporous sterilizing-agent or aerosol instead of hydrogen peroxide. Examples include oxonia and peracetic acid. A gaseous sterilizing-agent can also be used, such as for example ozone, in which case treatment steps will be adapted accordingly.

Figure 4:
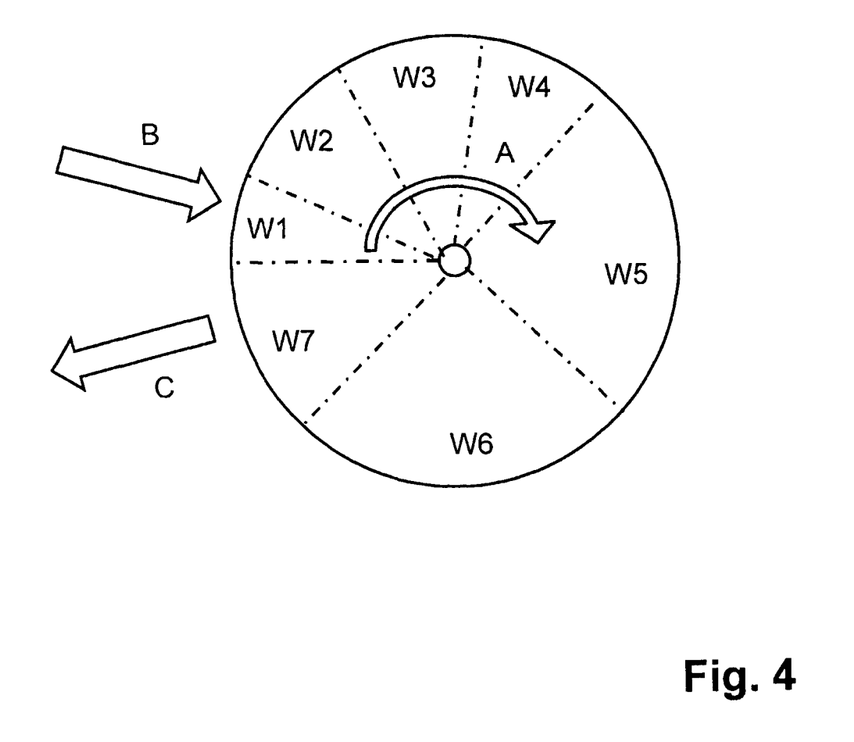
FIG. 4 shows a schematic representation to explain the different operations for the sterilization of seals performed solely in a single rotor.

FIG. 4 shows schematically the individual treatment steps during sterilization of seals 2. In this figure, angular ranges of the rotary motion of rotor 10 are indicated by W1-W7.

In a first angular region W1, seals 2 are fed to a seal-holder 11 at the seal-input 31 as indicated by arrow B. The first targeted and controlled application of $H_2O_2$ aerosol to the inside and outside of seals 2 is carried out in a second angular region W2 adjacent to the first angular region W1 in the downstream direction. The $H_2O_2$ aerosols act on the seals 2 in a third angular region W3 that is adjacent to the second angular region W2 in the downstream direction. This occurs at a waiting station 25. A renewed application of the $H_2O_2$ aerosol to the inside and outside of seals 2 takes place in a fourth angular region W4 that is adjacent to the third angular region W3 in the downstream direction. In the case of described seal-sterilizing device 1, angular regions W1, W2, W3 and W4 each correspond to one step of the cycled rotary motion of rotor 10.

A further acting of the sterilizing-agent on seals 2 takes place at the waiting stations 26 in a fifth angular region W5 that is adjacent to the fourth angular region W4 in the downstream direction. The fifth angular region W5 corresponds to four steps of the cycled movement of the rotor 10.

The application of seals 2 inside and outside with the hot activating-and-drying medium, preferably with the heated sterile air, is carried out in a sixth angular region W6 that is adjacent to the fifth angular region W5 in the downstream direction. In the case of the seal-sterilizing device 1, angular region W6 corresponds to six steps of the cycled movement of the rotor 10. The cooling and also the discharging of sterilized seals 2 at the seal-output 33 as indicated by arrow C then takes place at a cooling station 29 in a seventh angular region W7 which in the case of the seal-sterilizing device 1 corresponds to two steps of the rotary motion of the rotor 10.

Seals 2 do not always have the same diameter. If the nozzles 22 are aligned perfectly to strike the center of each seal, and the machine is to be used with different seals, the nozzles 22 will miss the centers of the new seals.

In order to ensure that the outlets and nozzles are always arranged substantially centrally/on the same axis as the seals even for changed seal diameters, e.g. from 38 mm diameter to seals of 28 mm diameter, i.e. that the jet of fluid (sterilizing-agent, activating-and-drying agent, cooling air/gas etc.) strikes the respective seal centrally and/or vertically, outlets or valves are held in guides so that the spacing between them can be made variable. Alternatively vertically neighboring outlets are disposed in an elongated carrier element that can be fitted to or removed from vertical legs of the corresponding treatment station as a format part.

In another embodiment, the liquid $H_2O_2$ or the $H_2O_2$-bearing solution is atomized in or through appropriate single- or twin-fluid nozzles and guided onto the seals. For this purpose the outlets 21 are designed accordingly or comprise such single- or twin-fluid nozzles, and the supply pipes and spraying-device/sections are adapted accordingly.

The invention has been described hereinbefore by reference to one embodiment. It goes without saying that this also encompasses a sterilization method which among other things uses the aforesaid device, and that furthermore variations as well as modifications are possible without departing from the inventive concept underlying the invention.

Regarding the sterilization method for seals, it is advantageous that the seals be guided vertically in seal-holders of a sterilization device and that, while in this stacked and uniformly aligned position, and without any further substantial movement relative to one another or to the holding element, the seals are moved as a group, step by step in angular increments, and positioned relative to the plurality of treatment stations, where they are treated before being conveyed onward.

Having described the invention, and a preferred embodiment thereof, what is claimed as new, and secured by Letters Patent is:

1. An apparatus for processing seals that are used for closing bottles, said seals having a diameter, said apparatus comprising a sterilizing machine for sterilizing said seals, said sterilizing machine comprising a transport system for moving said seals through treatment zones in which said seals are sterilized, activated, and dried, wherein said transport system comprises a seal input, a seal output, a rotor, a treatment path, a first application station, an activation and/or drying station, and seal holders, wherein said rotor rotates about a rotor axis in a rotation direction, wherein said seal holders are vertically oriented wherein said seal holders extend along a longitudinal direction, wherein said seal holders are disposed on a periphery of said rotor, wherein each of said seal holders accommodates a stack of seals, wherein each of said seal holders carries said stack of seals along said rotation direction through said treatment zones on said treatment path between said seal input and said seal output, wherein said first application station is on said treatment path, wherein said first application station comprises a first sterilizing-agent sprayer, wherein said first sterilizing-agent sprayer comprises successive outlets, wherein said outlets are spaced apart from each other in said longitudinal direction, wherein a distance between any pair of successive outlets is equal to said diameter, wherein said first sterilizing-agent sprayer is directed toward a seal holder for applying sterilizing agent onto individual seals held therein, and wherein said activating and/or drying station is provided downstream of said first application station in said rotation direction.

2. The apparatus of claim 1, wherein said application station further comprises a second sterilizing-agent sprayer, wherein said second sterilizing-agent sprayer is positioned opposite said first sterilizing-agent sprayer, wherein said first sterilizing-agent sprayer and said second sterilizing-agent sprayer are configured to apply sterilizing agent to opposite sides of individual seals that are held in a seal holder.

3. The apparatus of claim 1, further comprising at least a second application station for applying the sterilizing agent to seals that are held in seal holders, wherein said second application station follows said first application station in said rotation direction.

4. The apparatus of claim 3, wherein said seal holders are distributed about said rotor axis, wherein each pair of successive seal holders comprises seal holders separated by a fixed angular distance, and wherein each pair of successive application stations comprises application stations that are spaced apart by at least twice said fixed angular distance.

5. The apparatus of claim 3, further comprising a central sterilizing-agent supply, wherein said central sterilizing-agent supply interconnects outlets of sterilizing-agent spraying devices from different application stations.

6. The apparatus of claim 5, further comprising a waiting station, wherein said waiting station is disposed downstream of said application station and upstream of said activation and/or drying station in said rotation direction.

7. The apparatus of claim 5, further comprising a cooling station downstream of said activating and/or drying station in said rotation direction.

8. The apparatus of claim 1, wherein said rotor comprises a hollow drum, wherein said seal holders are arranged to form a cage, wherein said cage defines a drum jacket for said hollow drum, wherein said seal holders are configured to form said cage with rod-like seal guide rails, wherein said guide rails extend along said longitudinal direction, and wherein said guide rails are disposed to receive seals into said seal holders by having said seals pass between said guide rails.

9. The apparatus of claim 1, wherein said seal holders are oriented with their longitudinal directions parallel to said rotor axis.

10. The apparatus of claim 1, wherein said first sterilizing-agent sprayer is disposed to be lying inside along a trajectory of said seal holders, wherein said first sterilizing-agent sprayer does not circulate with either said seal holders or said rotor.

11. The apparatus of claim 1, wherein said first sterilizing-agent sprayer is disposed to be lying outside along a trajectory of said seal holders, wherein said first sterilizing-agent sprayer does not circulate with either said seal holders or said rotor.

12. The apparatus of claim 1, wherein said rotor defines a hollow drum, and wherein said apparatus further comprises central gas pipes and gas regulating devices connected to said gas pipes for gas and atmosphere management in an interior of said hollow drum.

13. A method for sterilizing seals, said method comprising at a seal input, placing a stack of seals in a vertically oriented seal holder on a periphery of a rotor that moves said seal holder, along with said seals, in a rotation direction along a treatment path, bringing said stack of seals to a first application station on said treatment path, at said first application station, directing sterilizing agent toward said seal holder for applying sterilizing agent onto individual seals held therein, wherein directing sterilizing agent comprises passing said sterilizing agent through successive outlets of a first sterilizing-agent sprayer, said outlets being spaced apart from each other by a seal diameter in said longitudinal direction, moving said stack of seals downstream along said rotation direction, activating or drying said stack of seals, and moving said stack of seals downstream to a seal outlet.

* * * * *